(12) United States Patent
Hatch

(10) Patent No.: US 10,722,260 B1
(45) Date of Patent: Jul. 28, 2020

(54) MODIFIED SURGICAL SCALPEL WITH POLYURETHANE MATED SHEATH: FOR ULTRASOUND ASSISTED CARPAL TUNNEL SURGERIES

(71) Applicant: Robert Hatch, Ormond Beach, FL (US)

(72) Inventor: Robert Hatch, Ormond Beach, FL (US)

( * ) Notice: Subject to any disclaimer, the term of this patent is extended or adjusted under 35 U.S.C. 154(b) by 357 days.

(21) Appl. No.: 14/075,120

(22) Filed: Nov. 8, 2013

Related U.S. Application Data

(62) Division of application No. 13/303,933, filed on Nov. 23, 2011, now Pat. No. 8,603,124.

(60) Provisional application No. 61/416,432, filed on Nov. 23, 2010.

(51) Int. Cl.
*A61B 17/32* (2006.01)

(52) U.S. Cl.
CPC ............... *A61B 17/320036* (2013.01)

(58) Field of Classification Search
CPC .............. A61B 17/320036; A61B 2017/00924
See application file for complete search history.

(56) References Cited

U.S. PATENT DOCUMENTS

| | | | |
|---|---|---|---|
| 3,906,626 A | 9/1975 | Riuli | |
| 4,962,770 A | 10/1990 | Agee | |
| 4,994,027 A | 2/1991 | Farrell | |
| 4,995,866 A | 2/1991 | Amplatz | |
| 5,029,573 A | 7/1991 | Chow | |
| 5,112,308 A | 5/1992 | Olsen | |
| 5,234,436 A * | 8/1993 | Eaton | A61B 17/320016 30/151 |
| 5,242,410 A | 9/1993 | Melker | |
| 5,312,360 A | 5/1994 | Behl | |
| 5,320,627 A | 6/1994 | Sorensen | |
| 5,391,177 A | 2/1995 | Schwartz | |
| 5,411,510 A * | 5/1995 | Fugo | A61B 17/3211 128/898 |
| 5,569,283 A | 10/1996 | Green | |
| 5,571,128 A * | 11/1996 | Shapiro | A61B 17/3211 606/167 |
| 5,620,454 A | 4/1997 | Pierce | |
| 5,662,669 A | 9/1997 | Abidin | |
| 5,665,099 A | 9/1997 | Pilo | |
| 5,735,865 A * | 4/1998 | Schaumann | A61B 1/317 600/101 |
| 5,868,771 A | 2/1999 | Herbert | |
| 6,007,554 A | 12/1999 | Van Ess | |
| 6,106,540 A | 8/2000 | White | |
| 6,530,902 B1 | 3/2003 | Jonkman | |

(Continued)

*Primary Examiner* — Julie A Szpira
(74) *Attorney, Agent, or Firm* — Erica M. Cipparone; Beusse, Wolter, Sanks & Maire, PLLC

(57) ABSTRACT

Devices, apparatus, and methods of using a modified scalpel tool that is removable from a polyurethane mated sheath for use in carpal tunnel surgeries and the like. The modified scalpel tool has an elongated stem with a flat blade at the distal end and an elongated handle at the proximal end. The sheath has a cavity for allowing the elongated blade to be inserted therein, two slots to receive two metal studs and a handle at its proximal end. The flat blade tool when combined (mated) with the polyurethane sheath produces a stable configuration that allows motion in only one rotational plane and with an arc of 90-95 degrees.

14 Claims, 16 Drawing Sheets

(56) References Cited

U.S. PATENT DOCUMENTS

| | | |
|---|---|---|
| 2003/0236506 A1 | 12/2003 | Schofield |
| 2004/0077987 A1* | 4/2004 | Rapacki ............ A61B 17/3468 604/8 |
| 2004/0087989 A1 | 5/2004 | Brenneman |
| 2005/0080443 A1 | 4/2005 | Fallin |
| 2005/0119680 A1 | 6/2005 | Dykes |
| 2006/0004398 A1 | 1/2006 | Binder, Jr. |
| 2006/0036270 A1 | 2/2006 | Terao |
| 2007/0106316 A1 | 5/2007 | Youssef |
| 2007/0208272 A1 | 9/2007 | Voegele |
| 2009/0125030 A1 | 5/2009 | Tebbe |
| 2009/0163942 A1 | 6/2009 | Cuevas |

* cited by examiner

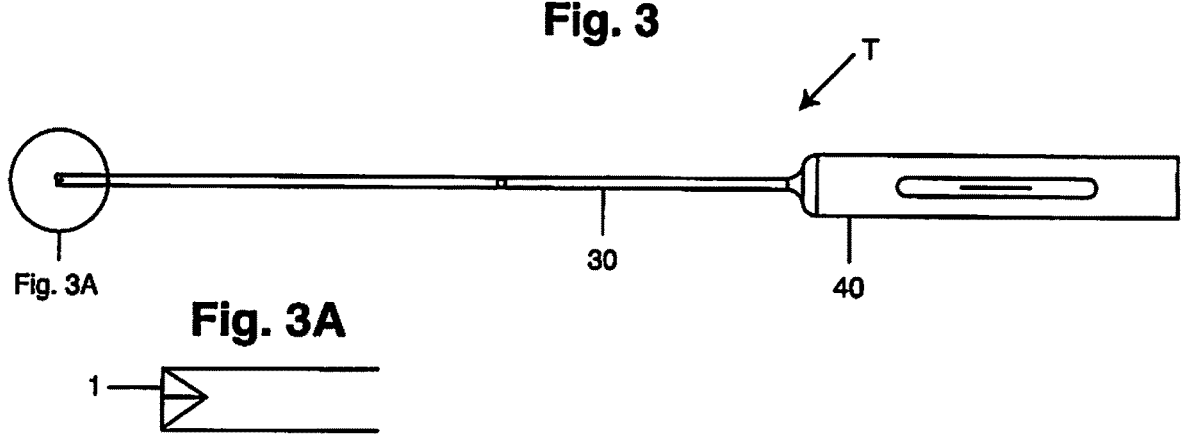
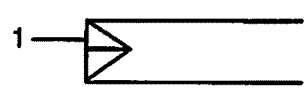
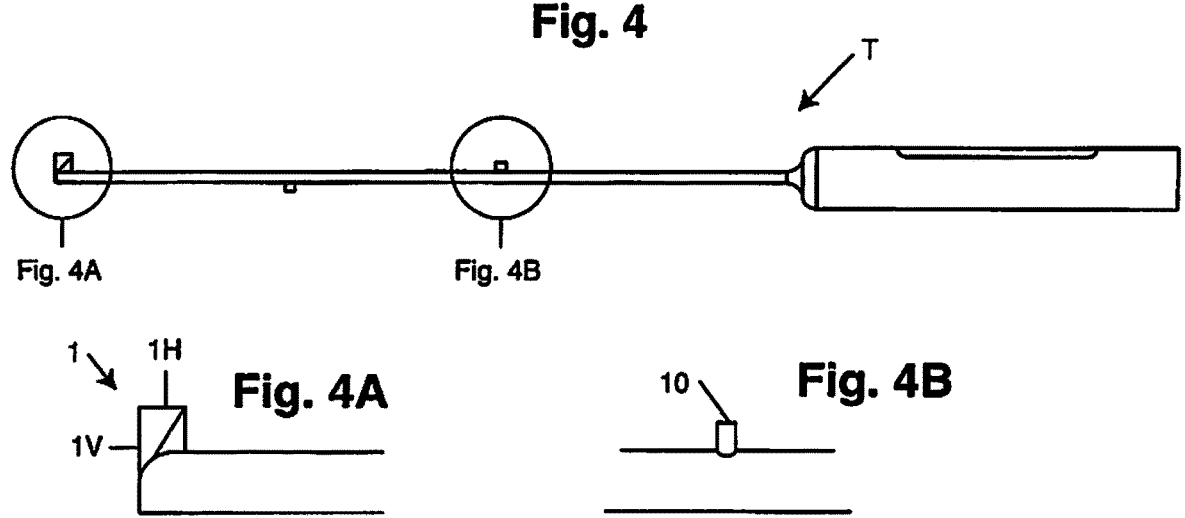
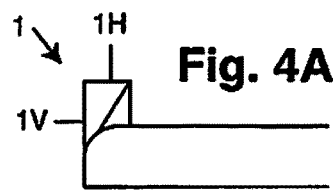
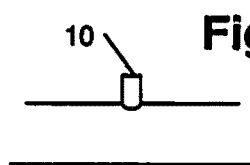

MODIFIED SURGICAL SCALPEL WITH POLYURETHANE MATED SHEATH: FOR ULTRASOUND ASSISTED CARPAL TUNNEL SURGERIES

This invention is a Divisional of U.S. patent application Ser. No. 13/303,933 filed Nov. 23, 2011, now allowed, which claims the benefit of priority to U.S. Provisional Patent Application Ser. No. 61/416,432 filed Nov. 23, 2010. The entire disclosure of each of the applications listed in this paragraph are incorporated herein by specific reference thereto.

FIELD OF INVENTION

This invention relates to surgical tools, and in particular to devices, apparatus, and methods of using a modified scalpel tool that fits within a polyurethane sheath for carpal tunnel surgeries and the like.

BACKGROUND AND PRIOR ART

Carpal tunnel syndrome often results in tingling, numbness, pain and hand weakness. The carpal tunnel is the narrow passageway on the palm side of one's wrist. This tunnel protects a main nerve (the median nerve) to the hand and nine tendons that flex fingers. Pressure placed on the portion of the median nerve inside the carpal tunnel has been known to produce the numbness, pain and, eventually, hand weakness that characterize the dysfunction caused by carpal tunnel syndrome.

Well known causes of this syndrome are repetitive use injury, traumatic injury of the hand and or wrist, metabolic conditions and by congenital or acquired physical characteristics of the carpal tunnel. Repetitive flexing and extending of the tendons in the hands and wrists, particularly when done forcefully and for prolonged periods without rest, can increase pressure within the carpal tunnel. Additionally, trauma to the wrist can cause swelling that exerts pressure on the median nerve. Physical characteristics may also cause the syndrome when a patient's carpal tunnel is more narrow than average.

Proper treatment by carpal tunnel surgery can relieve the pain and numbness and restore normal use of the wrist and hand. In most cases initial treatment consists of rest, activities modifications, use of non-steroidal anti-inflammatory agents and splints. Conditions resistant to conservative treatment and conditions considered too severe otherwise for conservative treatment are generally treated surgically by "carpal tunnel release." Carpal tunnel surgeries are usually done in hospital operating rooms by surgeons since these types of surgeries usually require the services of the anesthesia department, the operating room, and medical staff (surgeon, surgical assistance, nurses, etc). Additionally, lost work days during the patients recovery frequently adds costs that often exceed surgical costs.

As such, the initial surgical cost can be expensive, often up to $10,000 or more and there are estimated lifetime (lost work, surgical expenses, rehabilitation etc. . . . ) losses approaching $30,000 or more by some actuarial reports. Thus, with current methods such carpal tunnel conditions and subsequent surgery can be expensive and time consuming.

Various types of tools and devices have been designed for carpal tunnel surgery over the years with none as yet able to reduce expenses related to customary surgical expenses. Current surgeries either require a large (one centimeter or greater) surgical incision and/or utilize percutaneous tools placed without direct visualization of the delicate soft tissues. Large surgical incisions have the disadvantage of producing discomfort, and having longer recovery periods and postoperative surgical site sensitivity generally proportional to the length of the incision.

Accordingly, concepts of percutaneous surgery have become more widely accepted and utilized. In these procedures a small incision, usually between 7 mm and 1 cm, is made such that only specialized instrumentation may enter for the purpose of performing the necessary specific procedure. Current percutaneous procedures for carpal tunnel surgeries are performed endoscopically (ie, surgery with use of a small camera placed through the small incision to visualize the relevant anatomy while other instruments actively perform the procedure). Although these small incision techniques limit tissue injury they have a higher complication rate and are generally more expensive than other (open or "mini-open") methods.

Thus, the need exists for solutions to the above problems with the prior art.

SUMMARY OF THE INVENTION

A primary objective of the present invention is to provide devices, apparatus, systems and methods of performing hand surgeries, for carpal tunnel surgery where the procedure can be done by surgeons or properly trained non surgeons of different medical specialties, in an office setting using local anesthesia.

A secondary objective of the present invention is to provide devices, apparatus, systems and methods of performing hand surgeries, for carpal tunnel surgery, that can be done as an inexpensive procedure without the need for a hospital operating room, a hand surgeon, an anesthesiologist, and the like.

A third objective of the present invention is to provide devices, apparatus, systems and methods of performing hand surgeries, for carpal tunnel surgery, that can reduce the costs of carpal tunnel surgery by approximately 50%.

A fourth objective of the present invention is to provide devices, apparatus, systems and methods of performing hand surgeries, for carpal tunnel surgery, that results in decreased costs, improved safety, decreased complications and decreased tissue injury.

A fifth objective of the present invention is to provide devices, apparatus, systems and methods of performing hand surgeries, for carpal tunnel surgery introducing polyurethane material for ultrasound assisted surgeries to visualize the underlying instrument and underlying anatomic structures by decreasing a type of common imaging artifact called acoustic shadowing which is always present with metal objects (e.g. instrumentation), and which prevents accurate sonographic detection of nearby anatomic structures.

A sixth objective of the present invention is to provide devices, apparatus, systems and methods of performing hand surgeries for carpal tunnel surgery without a true incision which minimizes soft tissue surgical injury and speeds recovery resulting in a decrease in lost work hours.

Ultrasound applications for the diagnosis of carpal tunnel syndrome have been extensively published in refereed medical journals. Advanced ultrasound technology makes possible the visualization of the median nerve, its branches, the superficial arterial arch, and all tendons in and near the carpal tunnel and the transverse carpal ligament.

The subject novel invention encompasses instrumentation that can utilize ultrasound imaging technology for the purpose of safely performing surgical release of the transverse carpal ligament in an office setting by properly trained practitioners.

The use of polyurethane for ultrasound system procedures is a novel feature since the material is nearly invisible to ultrasound (i.e., sonolucent) allowing for better visualization of the cutting instrument and surrounding structures which improves the safety and accuracy of the procedure.

Polyurethane tools allow the surgeon to visualize what lies near and beneath the tool such as a complementary metal instrument or anatomic structures such as arteries, veins, nerves, muscle, tendons, and the like. The use of polyurethane allows for better visualization of the surgical target and vital surrounding structures while at the same time facilitating surgical dissection by housing and protecting the surgical area from the cutting tool while additionally being shaped at its end to easily slide adjacent to the median nerve and surrounding tendons. Thus, the shape of the assembled cutting tool and the use of polyurethane maximizes the ultrasound imaging technique while facilitating surgical dissection.

The modified surgical scalpel with the polyurethane sheath can be used in a medical procedure for treating carpal tunnel syndrome as will now be described. A 0.035 inch smooth guide pin can be placed alongside the median nerve by generally accepted techniques for needle placement ultrasound procedures. The pin is then pushed across the skin and fascia to the entrance of the carpal tunnel. A tissue dilator can be placed over the guide pin and then advanced into the carpal tunnel dilating the skin and fascia. The guide pin and the dilator are then removed.

The novel cutting blade with polyurethane sheath is assembled and placed into the wound created by the dilator. The cutting blade can be visualized with the polyurethane sheath and advanced to the distal transverse carpal ligament while the blade lies in a horizontal position (ie and perpendicular to the ultrasound wave) so that it can be optimally detected by the ultrasound machine.

The blade is then directed (turned) superficially toward the transverse carpal ligament by rotating the long handled blade 90 degrees. (Alternatively the blade can be advanced while in a vertical position and be "deployed" by rotating the sheath 90 degrees; this technique would require a metal marker be placed on the otherwise sonolucent polyurethane sheath so that a signal from the sheath surface could be detected while advancing through the carpal tunnel as the blade itself cannot be seen reliably while in a vertical position. Also alternatively the mirror image product of the polyurethane sheath also houses the same cutting blade and may be preferred for the opposite extremity depending on the surgeons technique preference as previously described).

Once the blade is deployed it is pressed "upward" through the transverse carpal ligament then pulled proximally cutting the transverse carpal ligament under direct vision, i.e., as seen on the ultrasound monitor. This procedure avoids injury to the delicate surrounding soft tissues such as the median nerve, the ulnar nerve and its accompanying artery, and the superficial arterial arch all of which are also seen on the ultrasound monitor during the procedure. A single stitch or tape closure can be applied to close the puncture wound.

Further objects and advantages of this invention will be apparent from the following detailed description of the presently preferred embodiments which are illustrated schematically in the accompanying drawings.

BRIEF DESCRIPTION OF THE FIGURES

FIG. 3 is a top view of the metal cutting tool of FIG. 2.
FIG. 3A is an enlarged view of the cutting edge blade of the tool of FIG. 2.
FIG. 4 is another side view of the metal cutting tool of FIG. 2.
FIG. 4A is an enlarged view of the cutting edge blade of the tool of FIG. 4.
FIG. 4B is an enlarged view of the locking stud portion of the tool of FIG. 4.

DESCRIPTION OF THE PREFERRED EMBODIMENTS

Figure 2:
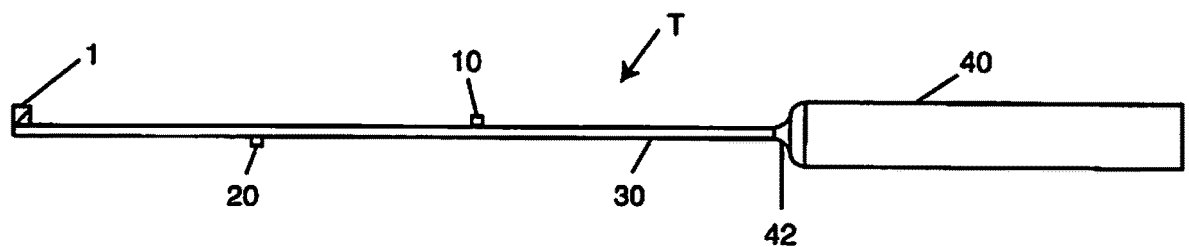
FIG. 2 is a side view of the metal cutting tool of FIG. 1

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

A list of components used in the figures is defined below.
1. cutting edge (blade)
10. locking stud
20. rotation stud
30. shaft of metal instrument
40. handle
42. handle tapers to shaft (stem)
50. tactile groove
60. trough for metal instrument (cutting edge, shaft)

Figure 1:
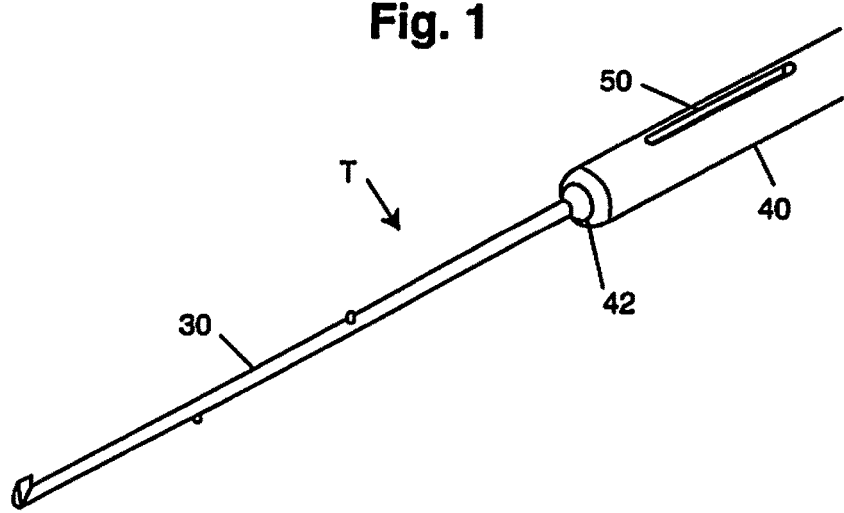
FIG. 1 is a perspective view of the novel metal cutting tool of the invention.

70. slot for rotation stud
80. slot for locking stud
90. handle
100. contoured end (for smooth dissection)
200. ultrasound transducer
300. entry device trocar
305. expanding diameter portion of trocar
310. guide pin
400. hand
410. skin puncture location Cutting Tool FIG. 1 is a perspective view of the novel metal cutting tool T, of the invention. FIG. 2 is a side view of the metal cutting tool T, of FIG. 1 FIG. 3 is a top view of the metal cutting tool T of FIG. 2. FIG. 3A is an enlarged view of the cutting edge (blade) 1 of the tool T, of FIG. 2. FIG. 4 is another side view of the metal cutting tool T of FIG. 2. FIG. 4A is an enlarged view of the cutting edge blade 1 of the tool of FIG. 4. FIG. 4B is an enlarged view of the locking stud portion 10 of the tool of FIG. 4.

Referring to FIGS. 1-4B, the novel metal cutting blade tool T, has a flat end blade 1, for maximum ultrasound signal returned, that can be made from stainless steel 17-4 and is designed for percutaneous transection of the transverse carpal ligament. The instrument T, can be inserted after proper soft tissue dilation. The handle 40 can have a cylindrical configuration with a maximum diameter of approximately 9 millimeters which continues along a length for approximately 55 mm and comprises the body of the handle 40. The handle 40 diameter then gradually tapers 42 to a diameter of approximately 1.5 to approximately 2 mm which forms the stem (shaft) 30 of the scalpel.

Along the stem 30 and approximately 65 mm from the blade-containing-end 1 of the stem can be an approximately 2 millimeter diameter raised stud 10 with a purpose to lock into a corresponding slot in the polyurethane sheath, S (described later on) thereby locking the scalpel tool T, into the sheath S.

A second (rotation) stud 20 can be placed approximately 30 mm toward the cutting end 1 from the first stud 10 and it is used to stop the blade 1 at 90 degrees of rotation from the starting position such that the blade 1 comes to an ideal cutting position.

A flat cutting blade 1 is located at the end of the stem (shaft) 30. The blade 1 can have a length of approximately 2.5 mm to approximately 3 mm and is located at the terminal 3 mm of the stem (shaft) 30. The height of the cutting blade 1 can measure approximately 2.5 mm. The blade 1 can have two cutting edges. One cutting edge 1V, can be the vertical edge for the handle 40 and the second cutting edge 1H, can be the horizontal edge adjacent to the vertical edge 1V. This 90° edge configuration allows for cutting action first "upward" through the transverse carpal ligament and then from distal to proximal along the transverse carpal ligament.

A tactile groove 50 can be located along a mid portion of the top of the handle 40 and can have a length of approximately 29 mm, and have a depth of approximately 1.5 mm. The tactile groove 50 can be placed on the handle 40 in line with the cutting blades sharp edge to provide tactile information for the surgeon about the position/orientation of the cutting edge.

The purpose of the tactile groove is to provide the surgeon with the exact spatial rotational orientation of the cutting edge. The surgeon can feel the groove and contemporaneously combine that known spatial orientation with what images are present on the display monitor. In the starting locked position, the tactile groove points horizontally relative to the sheath. During the portion of the procedure that advances the entire longitudinally the tactile groove allows the surgeon to know the plane of the cutting edge so that it is kept perpendicular to the plane of the transducer (which the surgeon sees at the surface of the palm) for best ultrasound detection.

Once the tool has reached the end of the transverse carpal ligament, the blade is unlocked and rotated to a vertical position. Without a reference such as the tactile groove the exact position of the cutting edge could not be reliably known since the detection of the blade becomes progressively faint and unreliable with increasing vertical orientation. Once the job of cutting the ligament is done the blade can then be returned by rotation back to the starting "safe" position.

Polyurethane Sheath

Figure 5:
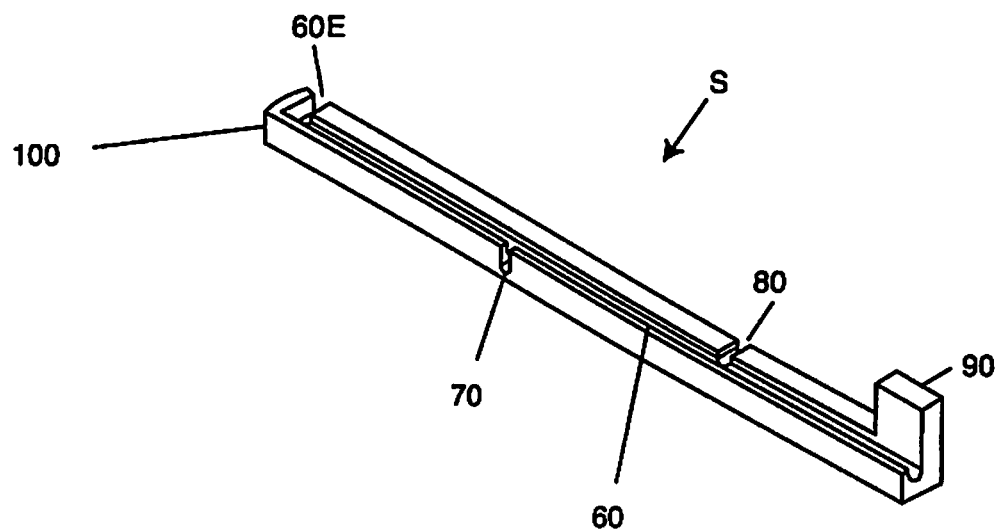
FIG. 5 is a perspective view of the polyurethane sheath used in the invention.
Figure 6:
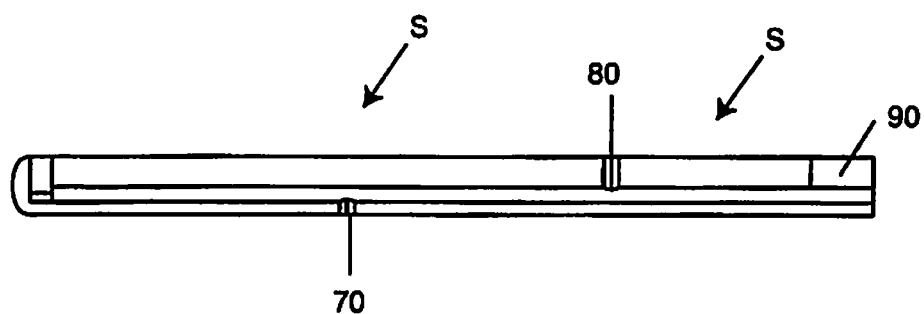
FIG. 6 is a top view of the polyurethane sheath of FIG. 5.
Figure 7:
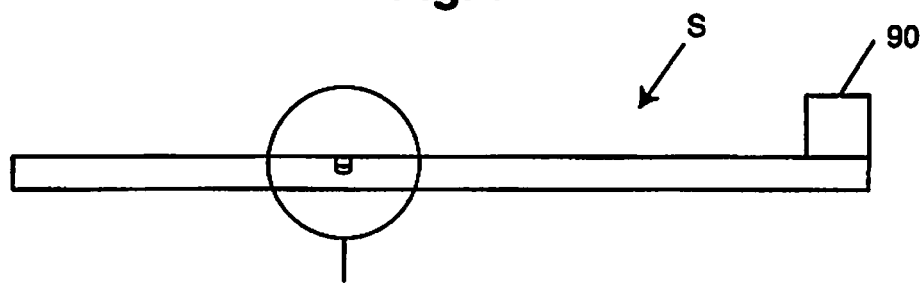
FIG. 7 is a side view of the polyurethane sheath of FIG. 6.
Figure 7A:
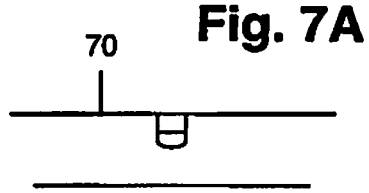
FIG. 7A is an enlarged view of the rotation stud slot portion of FIG. 7.

FIG. 5 is a perspective view of the polyurethane sheath S, used in the invention. FIG. 6 is a top view of the polyurethane sheath S, of FIG. 5. FIG. 7 is a side view of the polyurethane sheath S, of FIG. 6. FIG. 7A is an enlarged view of the rotation stud slot portion 70 of FIG. 7.

Referring to FIGS. 5-7A, the polyurethane sheath S, is designed to attach the novel metal cutting blade tool T and to complement the tool T, in such a way as to produce a smooth shaped design for blunt dissection to reach the surgical target. The purpose of the smooth shape is to safely deliver the cutting blade 1 to the site of action. Once the cutting blade 1 is at the site of action (in this case the transverse carpal ligament) the blade 1 is then rotated upward to a vertical position 90 degrees from the neutral/starting position while still lying within the sheath.

The sheath can be made from polyurethane for the purpose of its composition, which makes the sheath nearly invisible (sonolucent) to ultrasound waves. The relative invisibility allows the cutting tool T to be seen clearly and then be accurately placed at the intended site for surgery. The application can be varied widely for ultrasound assisted surgeries. The polyurethane design captures the rotational stud 20 in the rotation stud slot 70 and captures the locking stud 10 in the locking stud slot 80. The slots 70, 80 in the sheath S, snaps the studs 10, 20 in place and has a corresponding diameter slightly less than approximately 2 mm.

The sheath can be approximately 95 mm in length. A longitudinal trough 60 having a perpendicular end 60E having a width of approximately 2.5 mm, is used to supporting the shaft 30 and blade 1 of the tool T. The terminal portion of the opposite end of the cutting blade T can be flared to form a handle 90 to accommodate digital control. The handle 90 can have a height of approximately 7 mm and a width of approximately 7 mm.

The rotation stud slot 70 and locking stud slot 80 can have dimensions of approximately 1.0 to approximately 1.5 mm wide by approximately 1.25 to approximately 1.75 mm deep. The length between the locking stud slot 80 and the blade trough 60E can be approximately 65 mm, and the length between the rotation stud slot 70 and the blade trough 60E can be approximately 35 mm.

The portion 60E of the sheath S that houses the blade 1 can have a shape that can complement the blade 1 in such a way as to make a tubular shape of the composite instrument ideal for placement into the carpal tunnel. A contoured end 100 on the sheath S allows for a smooth dissection when the sheath S and tool T, are being used.

Figure 9:
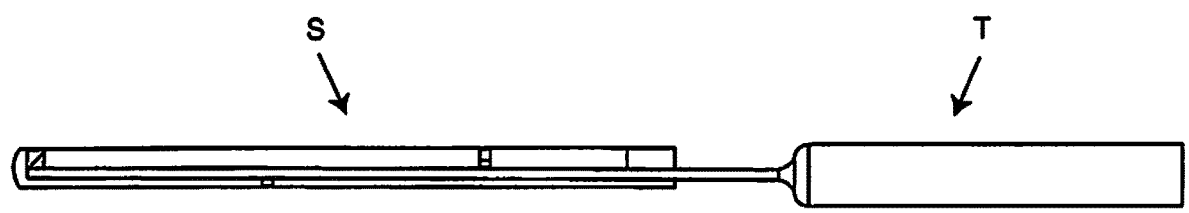
FIG. 9 is a top view of the blade with attached sheath of FIG. 8.
Figure 8:
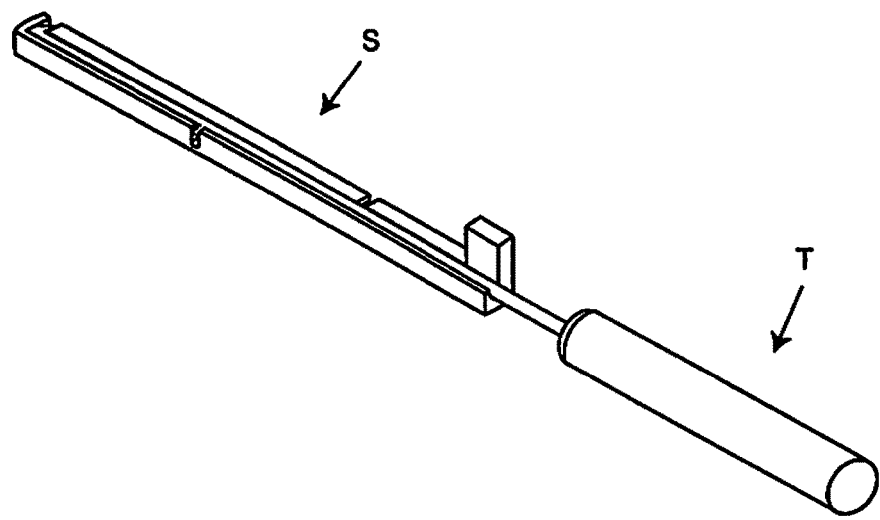
FIG. 8 is a perspective view of the blade end of the cutting blade tool of the preceding figures lying within and attached to the novel sheath of the preceding figures.
Figure 10:
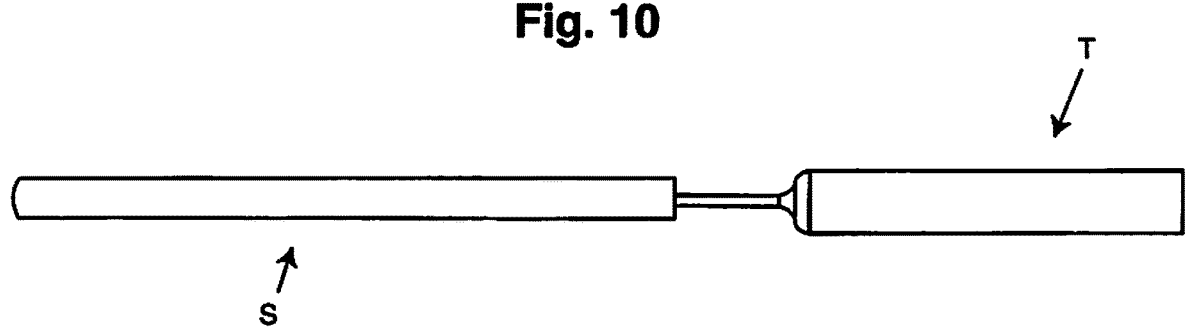
FIG. 10 is a bottom view the blade with attached sheath of FIG. 8.
Figure 11:
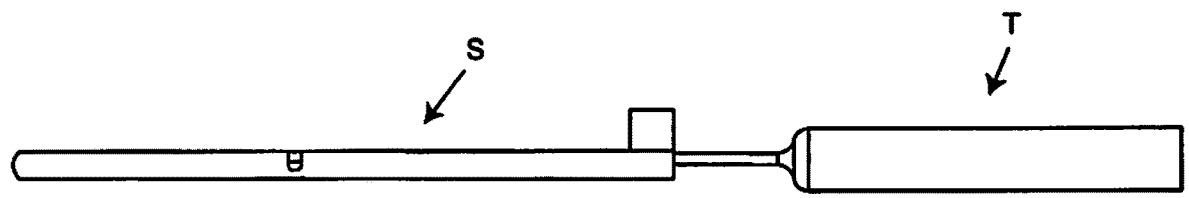
FIG. 11 is a side view of the blade with attached sheath of FIG. 8.
Figure 12:
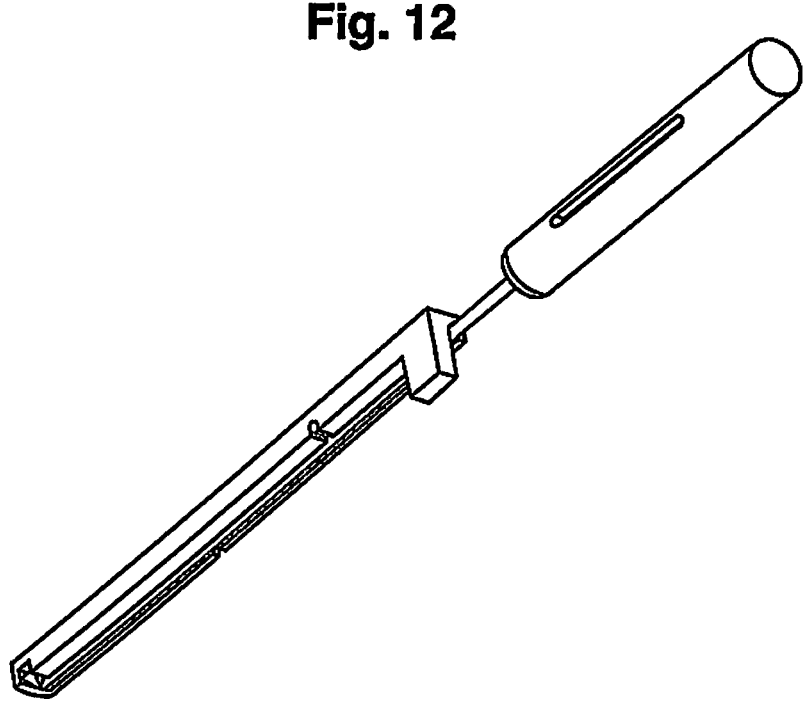
FIG. 12 is another perspective view of the blade tool T with attached sheath S of FIG. 8.

FIG. 8 is a perspective view of the blade end of the cutting blade tool T of the preceding figures lying within and attached to the novel sheath S of the preceding figures. FIG. 9 is a top view of the blade tool T with attached sheath S of FIG. 8. FIG. 10 is a bottom view the blade tool T with attached sheath S of FIG. 8. FIG. 11 is a side view of the blade tool T with attached sheath S of FIG. 8. FIG. 12 is another perspective view of the blade tool T with attached sheath S of FIG. 8.

Figure 14:
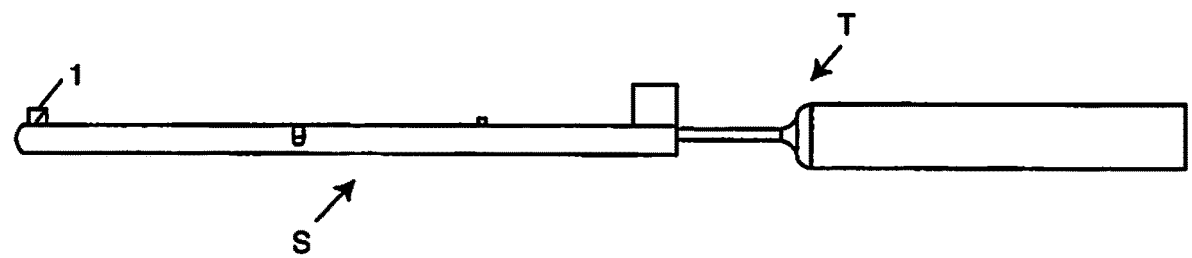
FIG. 14 is a side view of the blade tool T with attached sheath S, of FIG. 13 with the blade rotated to a cutting position.
Figure 13:
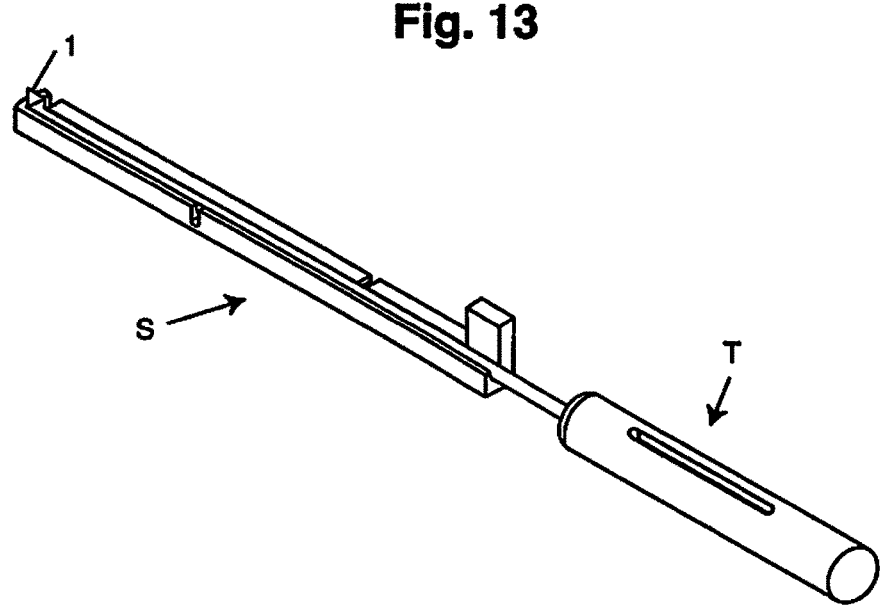
FIG. 13 is a perspective view of the blade tool T with attached sheath S with the blade rotated to a cutting position.
Figure 15:
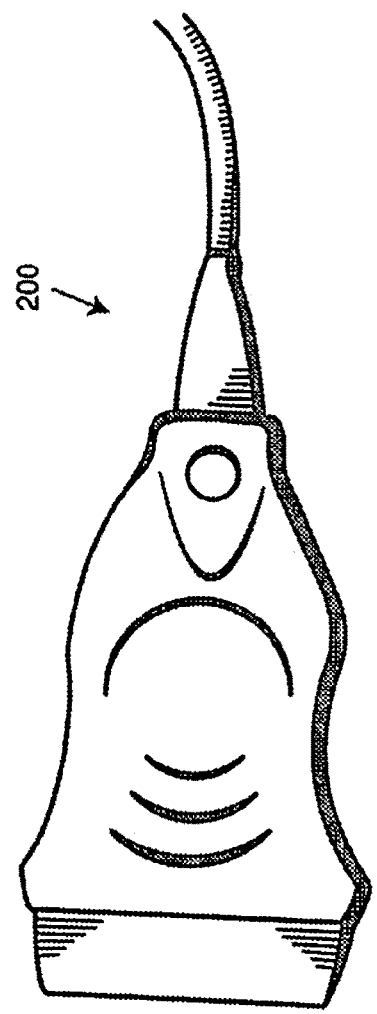
FIG. 15 shows an ultrasound machine/transducer that can be used with the invention.

FIG. 13 is a perspective view of the blade tool T with attached sheath S with the blade 1 rotated upward to a cutting position. FIG. 14 is a side view of the blade tool T with attached sheath S, of FIG. 13 with the blade 1 rotated to a cutting position. FIG. 15 shows an ultrasound machine/transducer 200 that can be used with the invention. A type of ultrasound transducer that can be used with the invention can be the GE Logiqe (CPU, display monitor and keyboard) mobile ultrasound unit with an attached RS-12L, 5-13 Mhz linear transducer probe.

For carpal tunnel surgery, the transducer is placed transversely over that portion of the carpal tunnel that needs to be seen. The transducer produces the sound that penetrates through the skin and deeper layers of the hand and then through the carpal tunnel to the bony surface at the bottom of the carpal tunnel. The ultrasound wave cannot penetrate bone. A computer processor then decodes the information from the return signal which provides information about the densities of the tissues at minute increments within the carpal tunnel. In this way the variation of the densities of the tissues within the carpal tunnel can be detected and projected as a gray scale image on the display monitor.

Similarly the high density of the metal tool can be detected relative to the surrounding anatomy and its structure can also seen clearly on the display monitor. The polyurethane sheath is sonolucent which means it has at best a faint signal and its form cannot be clearly seen. Additionally the polyurethane's sonographic invisibility allows the surgeon to view the structures immediately nearby (such as the median nerve and tendons) and maneuver the tool accordingly. Another advantage of the sheath's invisibility is to provide physical support to a relatively small piece of metal (ie the cutting tool) thereby minimizing artifact so that acoustic shadowing artifact from metal within the carpal tunnel is negligible.

Figure 16:
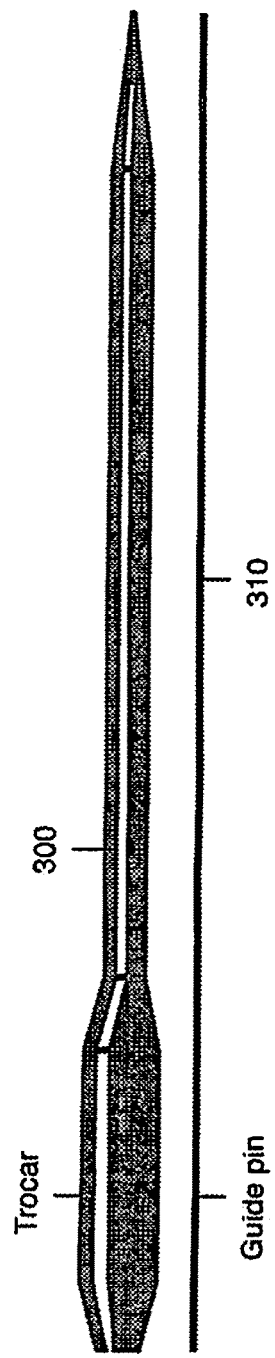
FIG. 16 shows a side view of a entry device (trocar) and guide pin that can be used with the invention.

FIG. 16 shows a side view of a entry device (trocar) 300 and guide pin 310 that can be used with the invention. The ultrasound transducer 200 along with the trocar 300 and guide pin 310 can be used with the novel cutting tool T and sheath S of the preceding figures for performing the percutaneous carpal tunnel surgery by ultrasound.

The trocar 300 used for experimentation with the invention was custom made by the inventor. The trocar 300 included a sharp cutting starting tip with smooth conical shaped dilation to a diameter of approximately 5.5 mm within a distance (from the tip) of approximately 1.5 cm and a continuous shaft and handle for manual control. The purpose of the trocar 300 is to gently dilate and expand the skin and fascial layers in preparation for the polyurethane sheath with cutting tool.

Figure 17:
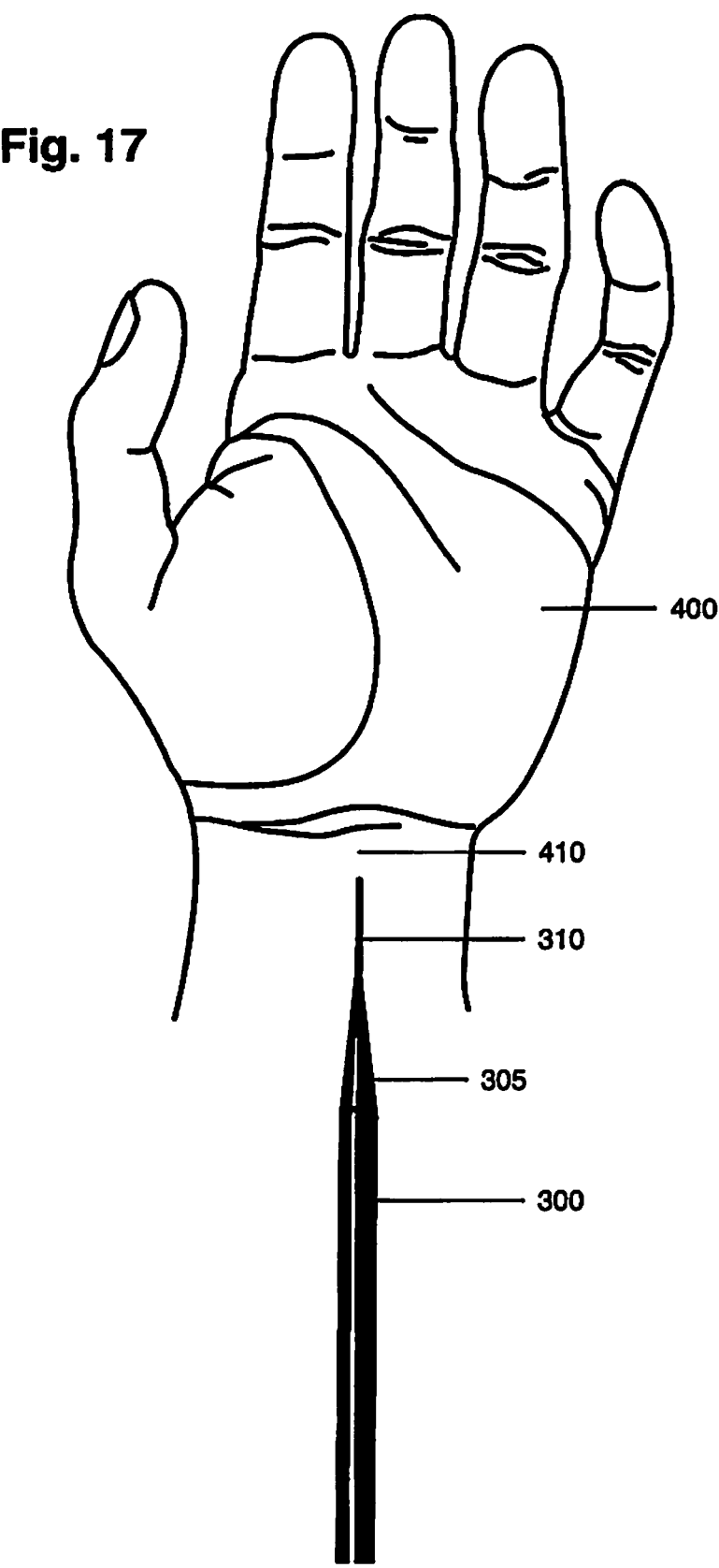
FIG. 17 shows a guide pin being readied for insertion to a hand.

FIG. 17 shows a guide pin 310 being readied for insertion to a hand 400. With ultrasound assistance and after sterile preparation of the hand 400 and distal forearm 410 a guide pin 310 (seen protruding from the trocar) punctures the skin 410 ulnar to the median nerve 1.5 cm proximal to the distal wrist crease. Standard ultrasound needle technique moves the guide pin 410 safely through the soft tissues to the proximal margin of the transverse carpal ligament. The ultrasound guided procedures is common in contemporary clinical practice. These procedures are performed by first visualizing the relevant anatomy and then under direct visualization using the ultrasound monitor display the needle is safely introduced and advanced to its target location. Since the guide pin 310 at approximately 0.035 is smaller than some needles it can similarly be placed using the same standard needle technique.

Figure 18:
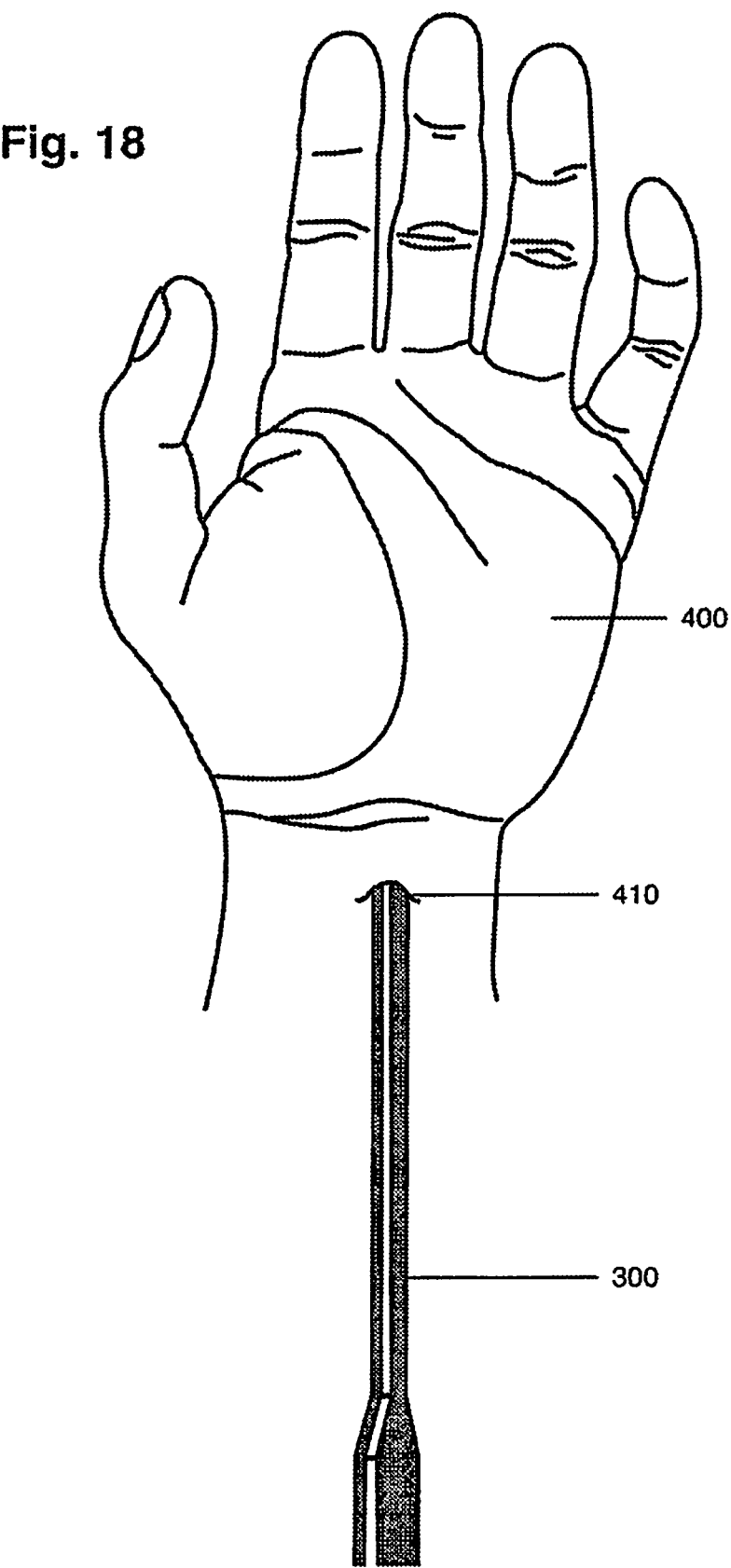
FIG. 18 shows the trocar being inserted into the hand.

Specifically for carpal tunnel use the needle (or guide pin) can be advanced toward the carpal tunnel from a starting point in the distal forearm while the median nerve is viewed transversely ie, with the transducer positioned in a perpendicular plane overlying the median nerve, and the needle (or guide pin) then advanced to the entrance of the carpal tunnel. FIG. 18 shows the guide pin 310 being inserted into the hand.

An alternative preparation for using the guide pin 310 begins by making a small puncture using a standard surgical blade and safe dissection technique through the forearm fascia followed by a hemostat or narrow blunt probe of the surgeon's choice.) The cannulated trocar then slides over the guide pin to the entrance of the carpal tunnel. Trocar 300 advancement along the path of the guide pin 310 avoids injury to the median nerve and the surrounding tendons by tracking along the guide pin.

With continued pressure the trocar 300 slowly advances until reaching the maximum diameter of up to approximately 5.5 mm. The expanding portion 305 of the trocar 300 safely expands the tissues in preparation for the medical tool T and should not be used to complete the dissection to the distal margin of the transverse carpal ligament.

Ultrasound imaging ensures safety of the median nerve and prevents excessive advancement of the guide pin and trocar during this part of the procedure. After the advancement, the guide pin 310 and trocar 300 are then removed.

Figure 19:
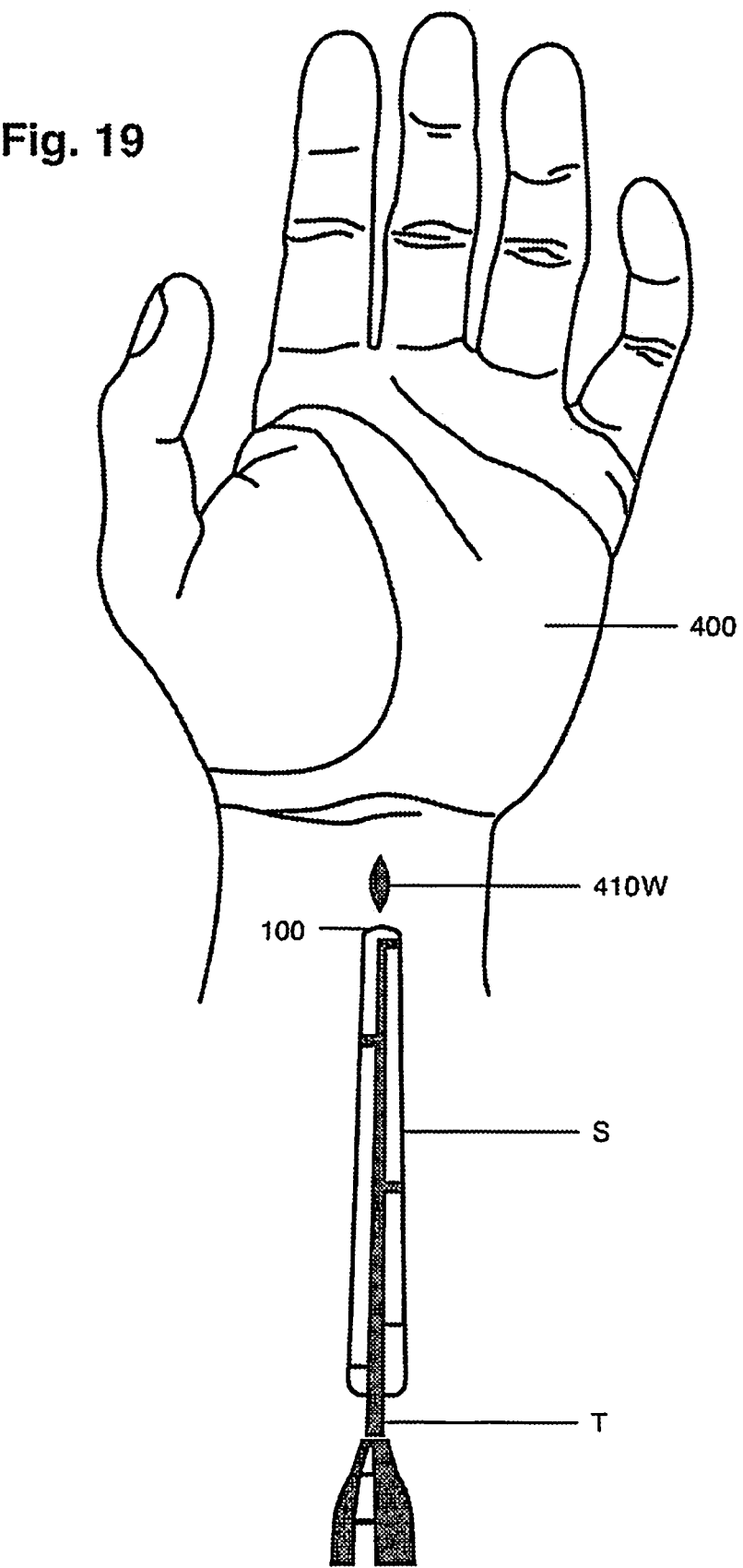
FIG. 19 shows the novel metal cutting tool with sheath being readied for use.

FIG. 19 shows the novel metal cutting tool T with sheath S being readied for use. The cutting end 100 of the medical tool T and sheath S should drop into the entry wound 410W with gentle pressure. The medical tool T and sheath S will follow the path of the trocar 310 beside the median nerve and then dissect further into the carpal tunnel with ultrasound imaging assistance from ultrasound transducer 200.

Figure 20:
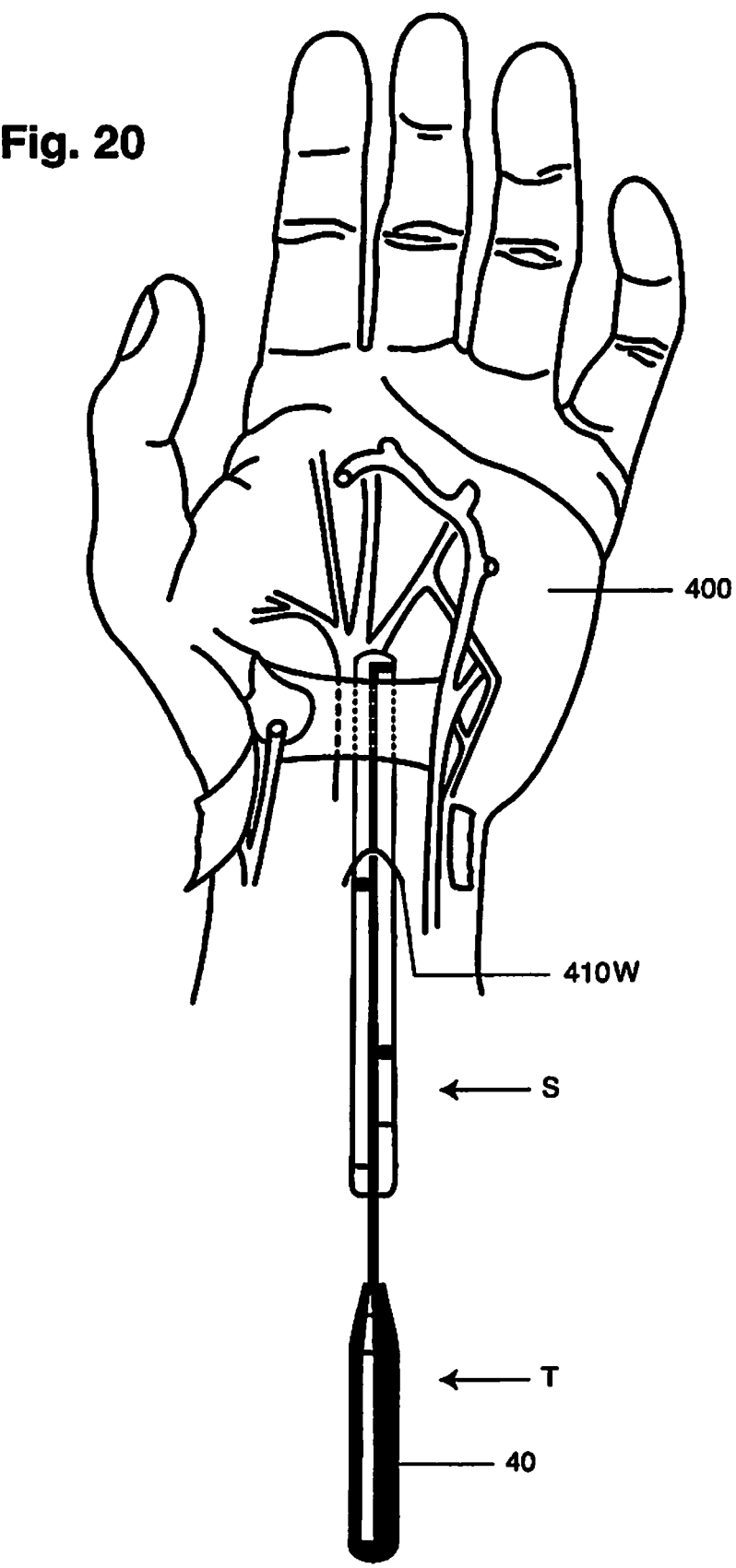
FIG. 20 shows the novel tool being inserted with the sheath into the hand.

FIG. 20 shows the novel tool T inserted with the sheath S into the hand 400. The medical tool T and S advances along the ulnar side of the median nerve and completes the dissection to the distal edge of the transverse carpal ligament. The hook of the hamate provides a good sonographic landmark for the distal margin of the transverse carpal ligament. The polyurethane sheath S prevents excessive acoustic shadowing (i.e. optimal visualization) of the nerve and ligament during the procedure.

The flat surface of the blade 1 maximizes ultrasound return signal and can be viewed on the image display relative to the hook of the hamate. Once reaching the end of the transverse carpal ligament the blade 1 rotates 90° clockwise to its cutting position by a turn of the metal handle 40 which frees the locking stud 10, FIGS. 1-4B, 13, and 14. Notably, the mirror image sheath design would require a counterclockwise turn to accomplish the same task of place the cutting edge at a vertical orientation from the locked/starting position.

The longitudinal score along the metal handle 40 in the plane of the cutting blade 1 is designed as a tactile reference to the blades' position when turning the handle 40 as this positional change of the blade 1 causes a significant decrease in ultrasound detection of the blade 1. The locking stud 10 also lies in the plane of the blade 1 and can be used for a visual reference to the blades position. At any time during the procedure the blade 1 can be rotated to the starting locked and protected position. To accomplish this task the sheath is held stationary by the surgeon or an assistant while the surgeon properly rotates the metal tool to the positions shown in FIGS. 13-14. The rotation stud allows motion in a 90 to 95 degree arc from the locked position to the cutting position. Since the metal tool/polyurethane sheath configuration locks the metal tool into the trough of the sheath combined with the geometries of the locking and rotation stud the metal tool moves only in a rotational plane as previously described. Any longitudinal push-pull forces by the surgeon moves the metal tool and polyurethane sheath as one stable/fixed unit. The spatial orientation of the sheath ideally is virtually unchanged during the entire procedure.

Figure 21:
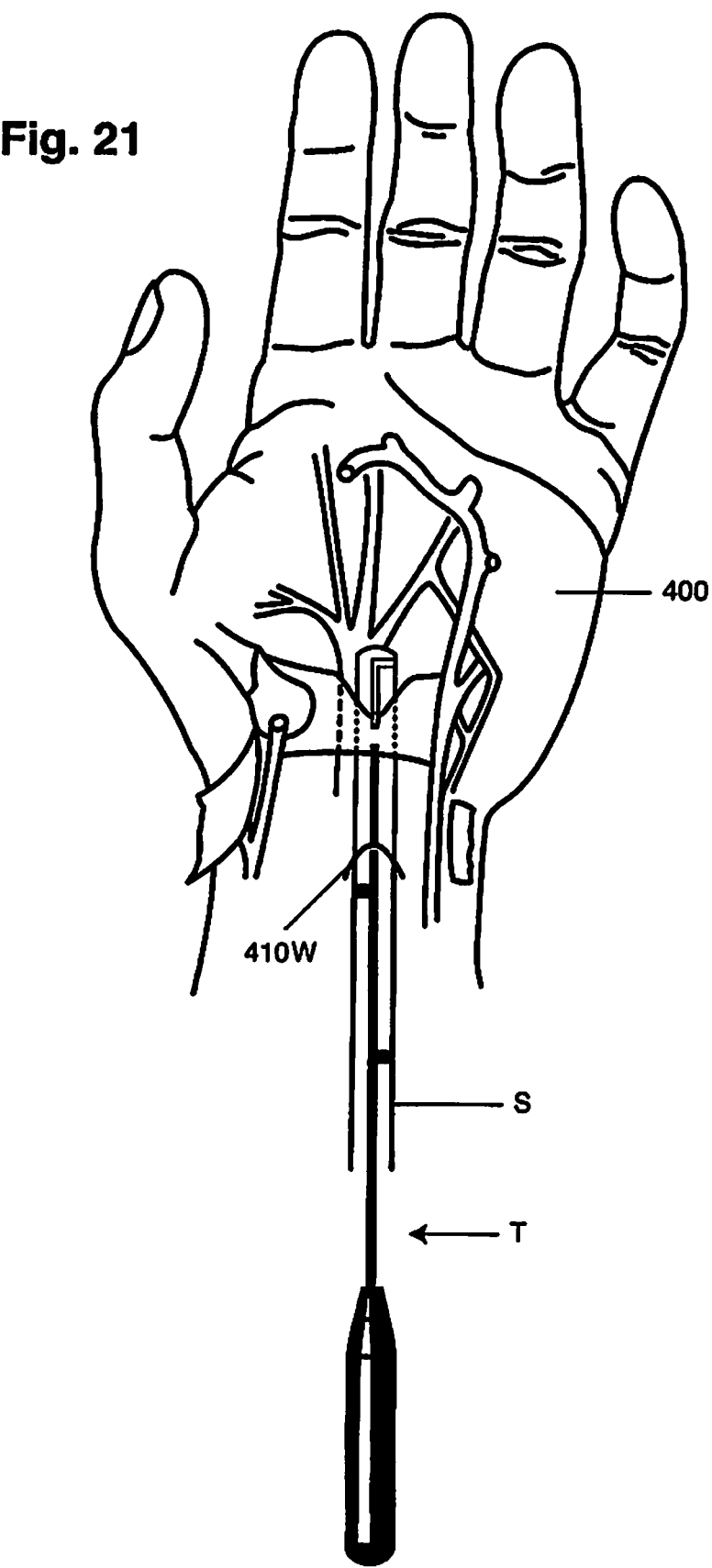
FIG. 21 shows the cutting position of the novel tool.

FIG. 21 shows the cutting position of the novel tool T. While in the cutting position, and as seen in FIGS. 13-14, upward pressure directs the blade 1 through the transverse carpal ligament. The blade 1 divides the transverse carpal ligament when pulled proximally.

Figure 22:
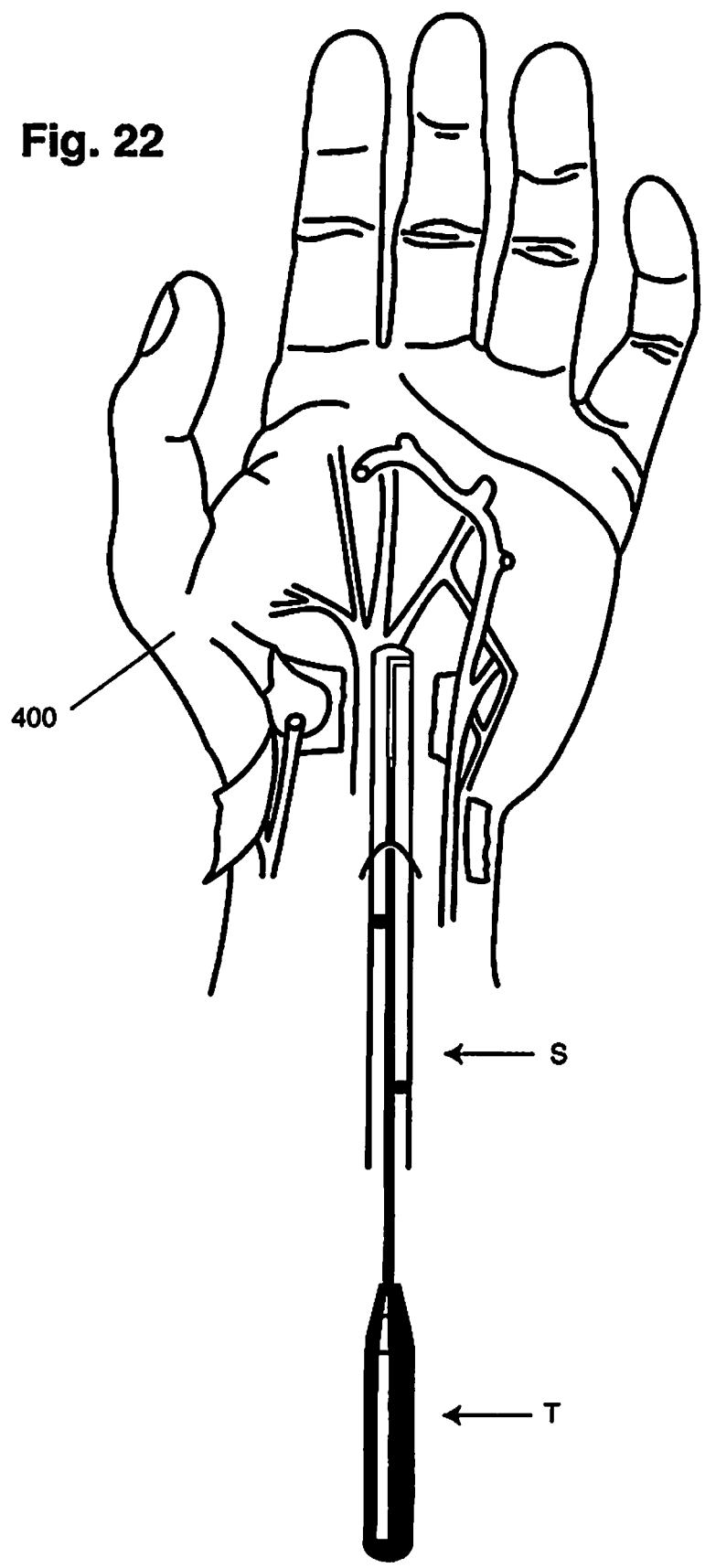
FIG. 22 shows the novel tool after cutting has occurred.

FIG. 22 shows the novel tool T after cutting has occurred. After ultrasound review of the completed transaction (of the transverse carpal ligament) the medical tool T should be rotated counter-clockwise (from FIGS. 13-14) to the locked position (FIGS. 8-12), and safely removed.

Figure 23:
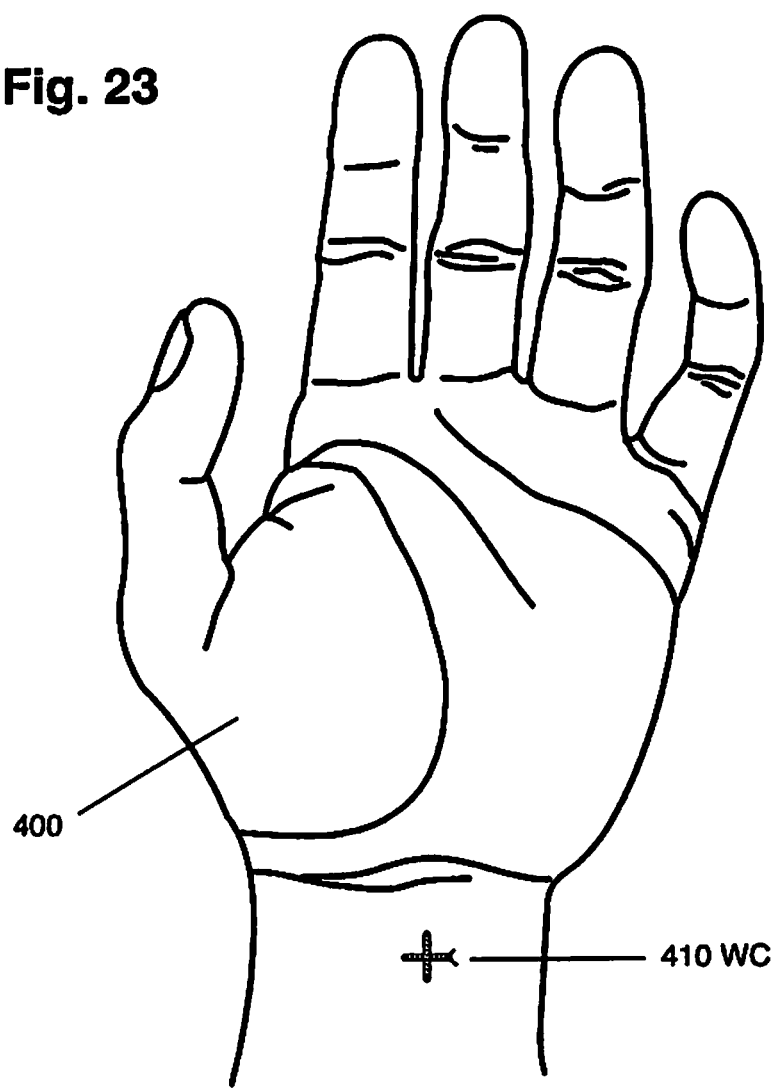
FIG. 23 shows the result where one final stitch is made to the hand.

FIG. 23 shows the result where one final stitch 410WC is made to the hand 400. One nylon stitch can close the entry wound after standard surgical wound management. A light dressing beneath a volar wrist splint covers the operative site and secures the hand.

While a preferred embodiment of the invention is described for carpal tunnel syndrome the invention can be used for other procedures. With minimal changes to the shape of the metal tool and polyurethane sheath, the novel invention can be used for other surgeries throughout the musculoskeletal system, such as but not limited to tarsal tunnel release.

The concept of ultrasound guided carpal tunnel release as well as attempts to produce the ideal tool are well documented in medical literature. In the journal of Bone Joint Spine 78 (2011) pp516-518 author Lecoq discusses the feasibility of percutaneous surgery under ultrasound guidance for carpal tunnel surgery. In 104 Cadaver wrists there was full release of the transverse carpal ligament using an arthroscopic trocar and a long handled knife.

Another minimally invasive technique for percutaneous carpal tunnel release by ultrasound guidance was published by author Rowe in the Annals of Plastic surgery Volume 55, Number 1, July 2005. The instrument used was designed for endoscopic surgery but successful release in six cadavers was achieved by ultrasound guidance.

In the Journal of Hand Surgery American 2010 March, 35 (3): 437-45 author Nakamichi submits evidence for a successful percutaneous carpal tunnel release using a retrograde approach (ie from distal to proximal) in a respectably large clinical trial with custom instrumentation designed specifically for the ultrasound guided approach.

Other percutaneous carpal tunnel release procedures have also been described using a needle to perforate/fenestrate the transverse volar carpal ligament followed by manual release. This approach serves as the most basic attempt at ultrasound guided transverse carpal ligament release. The common concept with all of these procedures is documented safe release of the transverse carpal tunnel ligament using an all metal instrument guided by ultrasound.

The subject invention was invented for percutaneous carpal tunnel release, specifically using a metal cutting tool with mated polyurethane sheath, and has been tested on two cadaver models. These unpublished experiments were done January 29,2010 and again Oct. 28, 2011. In the interim between the experiments the manufacturing was refined for the purpose of improving the cutting edge of the metal tool and to design a more fluid surgical sheath concept.

Both cadaver experiments were performed at the Hatch Orthopedics facility. Each specimen was received from the "Anatomic Gift Registry" company after the requisite (Florida) state approval for handling cadaveric tissue. The specimens were both freshly thawed embalmed female upper extremities (elbow, forearm, wrist and hand) with documented ages 63 and 44 years. Prior to surgical experimentation the specimens were radiographed to ensure normal boney anatomy and the soft tissues of the hand were then examined by ultrasound for review principally of the median nerve, the carpal tunnel and related structures. After documenting the predicted structure by x-ray and ultrasound the specimens were readied for the surgical procedure using the specialized instruments.

The Jan. 29, 2010 experiment used an "initial" prototype design where the sheath was pulled longitudinally along the shaft of the metal blade to uncover the blade. While this experiment was successful in targeting the correct carpal tunnel "safe zone" incision site and demonstrating the successful novel use of polyurethane in ultrasonic surgery the result was considered suboptimal due to the scoring and tearing from multiple passes of the relatively dull blade across the transverse carpal ligament. A second drawback of this initial configuration was the pull technique required to uncover the blade which caused unacceptable and somewhat awkward hand and instrument motion which, as a general surgical concept, could introduce unnecessary inaccuracy to the procedure. Thus, the second experiment introduced a modified design whereby either the blade or the sheath could be rotated 90 degrees from the other to begin cutting of the transverse carpal ligament.

More refined machining of the blade along with electropolishing made the metal blade appreciably sharper. These new modifications allowed precise control of the instrument during the procedure, introduced flexibility in the approach choice of the surgeon, ie whether to introduce the instrument with blade horizontal or vertical, and simplified the procedure by keeping the sheath attached to the blade at all times which allows for the blade to be rotated and thereby safely retracted whensoever desired during the procedure.

Although additional modifications to this design are planned the basic structure of the metal tool and polyurethane sheath concept is established. The thickness of the polyurethane sheath can be thinned to the limits and tolerances of the manufactured testing materials. Additionally, metal markers can be placed at the cutting end of the sheath to make the sheath ultrasonically visible from all practical rotational viewpoints. Furthermore, a hard polyurethane material may prove to be a considerably cheaper replacement of the metal tool. Still furthermore, an even sharper cutting edge (a slotted flat blade) can be incorporated into the polyurethane and should improve the cutting performance of the blade and accordingly further improve the control of the instrument by the surgeon.

After both surgical experiments a complete dissection of the median nerve and the carpal tunnel were performed. In both experiments the pre-surgical diagnostic sonographic information accurately predicted and otherwise correlated well with the actual underlying/dissected anatomic structure of the specimens.

Using the modified prototype blade and sheath the October 28,2011 experiment documents complete release of the transverse carpal ligament in an arguably more refined and reliable fashion than that previously described in the medical literature. With these experiments, there was no damage to the median nerve or its branches, carpal tunnel tendons, and ulna neurovascular bundle. The transverse carpal ligament was released with ideal minimal penetration into the more superficial overlying layers of the palmar fascia.

The modified blade and sheath concept achieved the goal of successful percutaneous carpal tunnel release in a clinical setting and supports the prediction as described by Rowe (in the discussion portion of his cadaver study) when he states, "this technique has the potential to increase safety of the carpal of the carpal tunnel release, further decrease its morbidity, shorten the post-operative recovery time, and lower costs by offering the procedure in an office setting".

Although the embodiment described above, uses a polyurethane sheath, the invention can be practiced with other types of materials and compositions that can have similar functionality to the polyurethane sheath as described above.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A medical instrument for repairing carpal tunnel syndrome, comprising:
    a carpal tunnel repairing tool having a proximal end and a distal end, the tool comprising a shaft extending between a handle at the proximal end and a blade at the distal end, wherein the blade is a perpendicular planar extension of at least a portion of the shaft;
    a sheath for receiving at least a portion of the carpal tunnel repairing tool, the sheath comprising a longitudinal trough for receiving at least a portion of the shaft, and a blade trough for receiving the blade;
    wherein rotation of the shaft cooperatively rotates the blade relative to the sheath, such that the tool is rotatable between a first position and a second position, wherein when the tool is in the first position, the blade is received within the blade trough, and wherein when the tool is in the second position, the blade is released from the blade trough to a cutting position, exposed for use,
    wherein the tool further comprises one or more studs extending from a surface thereof, and the sheath comprises one or more notches for receiving the one or more studs of the tool during use of the instrument, wherein an interface between at least a first stud and cooperating first notch is configured to prevent movement of the tool along a longitudinal axis relative to the sheath during placement and removal of the instrument into a hand of a patient;
    wherein an interface between at least a second stud and a cooperating second notch is configured to limit rotation of the tool relative to the sheath when the tool is rotated from the first position to the second position, and wherein movement of the tool along a longitudinal axis relative to sheath is prevented.

2. A medical instrument for repairing carpal tunnel syndrome, comprising:
    a carpal tunnel repairing tool having a proximal end and a distal end, the tool comprising a shaft extending between a handle at the proximal end and a blade at the distal end, wherein the blade is a perpendicular planar extension of at least a portion of the shaft;
    a sheath for receiving at least a portion of the carpal tunnel repairing tool, the sheath comprising a longitudinal trough for receiving at least a portion of the shaft, and a blade trough for receiving the blade;
    wherein rotation of the shaft cooperatively rotates the blade relative to the sheath, such that the tool is rotatable between a first position and a second position, wherein when the tool is in the first position, the blade is received within the blade trough, and wherein when the tool is in the second position, the blade is released from the blade trough to a cutting position, exposed for use, wherein when the tool is in the second position, a plane of the blade is substantially perpendicular to the plane of the sheath.

3. The medical instrument of claim 1, wherein when the tool is in the first position, the one or more studs are received within the one or more notches, restricting longitudinal and/or rotational movement of the tool relative to the sheath.

4. The medical instrument of claim 2, further comprising wherein at least a portion of the sheath comprises a sonolucent material.

5. A medical instrument for repairing carpal tunnel syndrome, comprising:
    a carpal tunnel repairing tool having a proximal end and a distal end, the tool comprising a shaft extending between a handle at the proximal end and a blade at the distal end, wherein the blade is a perpendicular planar extension of at least a portion of the shaft;
    a sheath for receiving at least a portion of the carpal tunnel repairing tool, the sheath comprising a longitudinal trough for receiving at least a portion of the shaft, and a blade trough for receiving the blade;
    wherein rotation of the shaft cooperatively rotates the blade relative to the sheath, such that the tool is rotatable between a first position and a second position, wherein when the tool is in the first position, the blade is received within the blade trough, and wherein when the tool is in the second position, the blade is released from the blade trough to a cutting position, exposed for use,
    wherein the handle further comprises a tactile groove substantially aligned along a vertical plane with the longitudinal axis of the blade, so as to provide a spatial orientation of the blade during use of the instrument in a patient.

6. The medical instrument of claim 1, wherein when the tool is in a first position, the blade is secured in a non-cutting position for safe delivery and removal of the instrument to a cutting position.

7. A medical instrument for repairing carpal tunnel syndrome, comprising:
    a carpal tunnel repairing tool having a proximal end and a distal end, the tool comprising a shaft extending between a handle at the proximal end and a blade at the distal end, wherein the blade is a perpendicular planar extension of at least a portion of the shaft;
    a sheath for receiving at least a portion of the carpal tunnel repairing tool, the sheath comprising a longitudinal trough for receiving at least a portion of the shaft, and a blade trough for receiving the blade;
    wherein rotation of the shaft cooperatively rotates the blade relative to the sheath, such that the tool is rotatable between a first position and a second position, wherein when the tool is in the first position, the blade is received within the blade trough, and wherein when the tool is in the second position, the blade is released from the blade trough to a cutting position, exposed for use, wherein the blade comprises a first vertical cutting edge and a first horizontal cutting edge, wherein the first vertical cutting edge is perpendicular from the first horizontal cutting edge.

8. The medical instrument of claim 1, wherein the first and second studs are substantially 180 degrees apart from one another.

9. The medical instrument of claim 4, wherein the sheath comprises a polyurethane material.

10. The medical instrument of claim 2, wherein the sheath shields the blade from surrounding tissue of a patient during placement and removal of the instrument from a hand of the patient.

11. A method of using a medical instrument for repairing carpal tunnel syndrome, comprising:
   a carpal tunnel repairing tool having a proximal end and a distal end, the tool comprising a shaft extending between a handle at the proximal end and a blade at the distal end, wherein the blade is a perpendicular planar extension of at least a portion of the shaft;
   a sheath for receiving at least a portion of the carpal tunnel repairing tool, the sheath comprising a longitudinal trough for receiving at least a portion of the shaft, and a blade trough for receiving the blade;
   wherein rotation of the shaft cooperatively rotates the blade relative to the sheath, such that the tool is rotatable between a first position and a second position, wherein when the tool is in the first position, the blade is received within the blade trough, and wherein when the tool is in the second position, the blade is released from the blade trough to a cutting position, exposed for use; and
   wherein the instrument is inserted into the entry site in a hand of a patient at a position proximal to a transverse carpal ligament until the blade extends beyond the distal edge of the transverse carpal ligament, wherein during the insertion step, the tool is in a first position relative to the sheath; wherein the tool is rotated to a second position by rotation of the handle to expose the blade to the cutting position while maintaining the position of the sheath, and wherein the transverse carpal ligament is cut by applying upward pressure to direct the blade through the transverse carpal ligament and moving the instrument in a proximal direction to sever the transverse carpal ligament; wherein the tool is rotated to the first position by rotation of the handle; and the instrument is removed from the patient.

12. The method of claim 11, further comprising inserting a guide pin into the entry site and moving the guide pin to a proximal margin of a transverse carpal ligament, wherein insertion of the guide pin occurs prior to the insertion of the instrument step.

13. The method of claim 12, wherein the guide pin is inserted during visualization of the guide pin with an ultrasound machine.

14. The method of claim 12, further comprising inserting a trocar over the guide pin to an entrance to the carpal tunnel to expand tissues of the patient prior to insertion of the tool.

* * * * *